(12) United States Patent
Adamski et al.

(10) Patent No.: US 8,442,179 B2
(45) Date of Patent: May 14, 2013

(54) METHOD AND APPARATUS FOR TAGGING AND IDENTIFYING A TARGET

(75) Inventors: John L. Adamski, Kenmore, WA (US);
Richard H. Bossi, Renton, WA (US);
James M. Nelson, Sumner, WA (US);
William G. Bartholet, Issaquah, WA (US)

(73) Assignee: The Boeing Company, Chicago, IL (US)

( * ) Notice: Subject to any disclaimer, the term of this patent is extended or adjusted under 35 U.S.C. 154(b) by 718 days.

(21) Appl. No.: 11/875,530

(22) Filed: Oct. 19, 2007

(65) Prior Publication Data
US 2009/0304152 A1    Dec. 10, 2009

(51) Int. Cl.
*G21G 1/12*    (2006.01)
*G01T 1/161*    (2006.01)

(52) U.S. Cl.
USPC .......................... 376/157; 250/303; 376/153

(58) Field of Classification Search ................... 376/153, 376/157; 250/303
See application file for complete search history.

(56) References Cited

U.S. PATENT DOCUMENTS

| | | | |
|---|---|---|---|
| 3,517,195 A * | 6/1970 | Leavitt .......................... | 378/124 |
| 3,924,125 A * | 12/1975 | Murray ......................... | 250/303 |
| 4,731,531 A | 3/1988 | Handke | |
| 5,175,756 A * | 12/1992 | Pongratz et al. ................ | 378/88 |
| 6,740,875 B1 * | 5/2004 | Ishikawa et al. .............. | 250/302 |
| 2004/0024060 A1 * | 2/2004 | Lundstedt et al. ............. | 514/554 |

* cited by examiner

*Primary Examiner* — Johannes P Mondt
(74) *Attorney, Agent, or Firm* — Alston & Bird LLP

(57) ABSTRACT

A method and apparatus for identifying and tagging a target, such an individual or an item, are described that provide an improved mechanism for identifying the target without alerting the target. In this regard, a method and apparatus can irradiate the target so as to create a radioisotope signature for the target. By thereafter monitoring the radioisotope signature, the target can be identified and tracked in a covert manner.

17 Claims, 2 Drawing Sheets

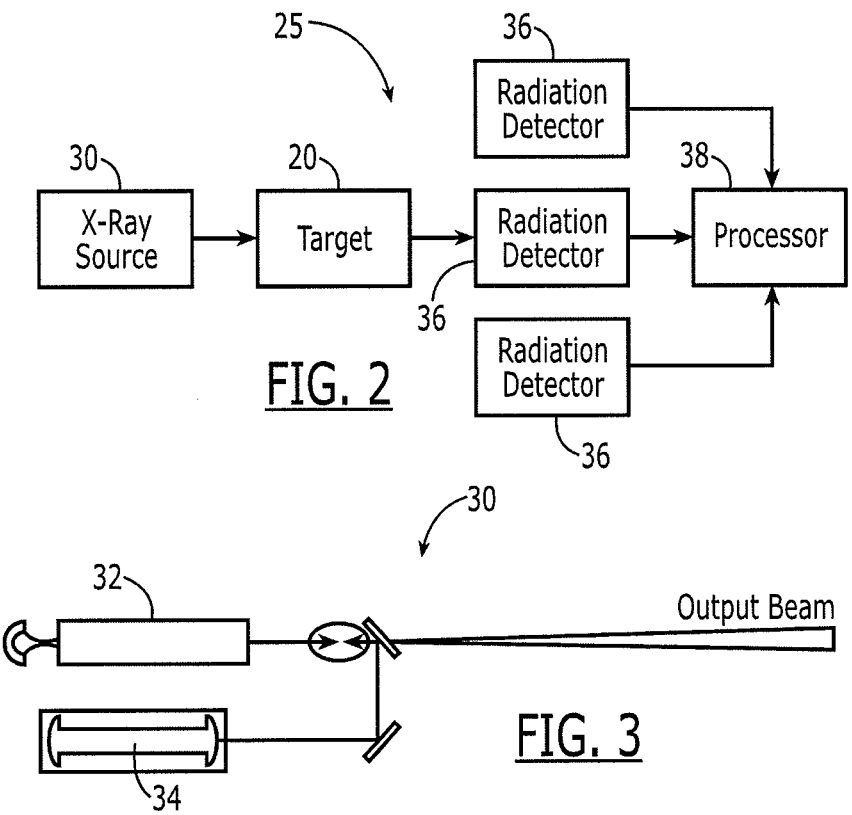
FIG. 2
FIG. 3
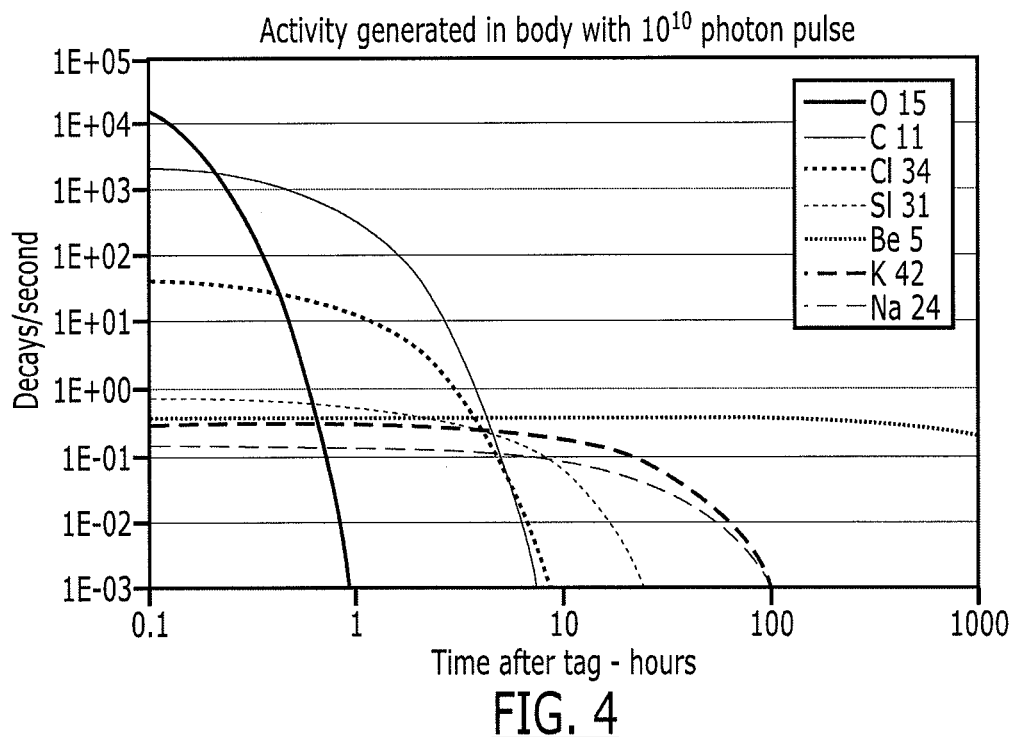
FIG. 4

METHOD AND APPARATUS FOR TAGGING AND IDENTIFYING A TARGET

FIELD OF THE INVENTION

Embodiments of the present invention relates generally to methods and apparatus for tagging and identifying a target and, more particularly, to methods and apparatus for tagging and identifying a target based upon a radioisotope signature of the target.

BACKGROUND OF THE INVENTION

It is desirable in a number of applications to be able to identify a person or an item and to thereafter track the person or item. For example, a number of military, intelligence and/or law enforcement agencies may desire to identify and track individuals or items for security purposes or to otherwise gather information about the individuals or items as well as the route or path of travel of the individuals or items.

In one common example, an individual can be identified and, to some degree, tracked by identifying the individual at each of a plurality of security checkpoints, such as those located in airports, along borders and the like. At such security checkpoints, an individual is generally required to provide a means of identification, such as a driver's license, a passport or the like. Similarly, items may be identified and tracked by gathering information about the items being shipped into or out of a country during a border inspection or the like. As will be apparent, however, the tracking afforded by such techniques is relatively limited and consists merely of the identification of the individual at one or more discrete locations with little or no information provided regarding the travel of the individual between those discrete inspection stations. Additionally, such conventional techniques for identifying an individual require the participation of the individual and, as such, are not generally performed surreptitiously, as would be desired in some instances, such as in some military, intelligence and such or law enforcement contexts.

One alternative technique for identifying and tracking an individual or an item has been proposed in which tags may be mechanically affixed to an item including, for example, an item carried by or otherwise associated with an individual. For example, a vehicle driven by an individual may be tagged. In accordance with this technique, the tags that are mechanically affixed to an item may be optically interrogated in order to locate and track the item. Since the tags must be physically attached to the item, the tags are generally unable to locate and track an individual in as robust a manner as desired with the technique being unable to locate and track the individual in those instances in which an individual does not carry an item that has been tagged or is not riding in a vehicle that has been tagged. Additionally, it may be difficult, if not impossible, to mechanically affix the tags to the item in a surreptitious manner as would be desired in some instances, such as in the context of military, intelligence and/or law enforcement activities.

Accordingly, it would be desirable to provide an improved method and apparatus for identifying, locating and tracking individuals or items without alerting or otherwise imposing upon the individual.

BRIEF SUMMARY OF THE INVENTION

A method and apparatus for identifying and tagging a target, such an individual or an item, are described that provide an improved mechanism for identifying the target without alerting the target. In this regard, a method and apparatus according to one embodiment can irradiate the target so as to create a radioisotope signature for the target. By thereafter monitoring the radioisotope signature, the target can be identified and tracked in a covert manner.

In one aspect of the present invention, a method of identifying a target is provided in which the target is tagged with a radioisotope signature. In this regard, the target may be irradiated with an x-ray pulse to create one or more radioisotope species within the target. The one or more radioisotopes species within the target define the radioisotope signature for the target. Thereafter, the target may be identified by comparing radiation emitted by the target with the radioisotope signature with which the target is tagged. For example, radiation emitted by the target may be detected and then compared with the radioisotope signature to permit identification of the target. In one embodiment, the radiation emitted by the target may be detected at a plurality of different locations. As such, the target may be tracked by identifying the target in response to the radiation detected at each of the plurality of different locations.

In one embodiment, the target may be irradiated with a plurality of x-ray pulses having different energy levels which collectively create one or more radioisotope species that define the radioisotope signature. By utilizing a plurality of x-ray pulses, the resulting radioisotope signature can be further tailored to insure uniqueness. In one embodiment, the target may be irradiated with a monochromatic x-ray pulse. The x-ray pulse may also be relatively short in duration, such as by having a full wave half maximum (FWHM) duration of no more than 10 picoseconds. Further, the flux of each x-ray pulse may be controlled and has a flux of at least $1 \times 10^9$ photons and an energy of at least 15 MeV in one embodiment.

In accordance with another aspect of the present invention, an apparatus for tagging and identifying the target is provided that includes an x-ray source for irradiating the target with an x-ray pulse. The x-ray pulse creates one or more radioisotopes species within the target which, in turn, define the radioisotope signature of the target. In one embodiment, the x-ray sources is configured to irradiate the target with a plurality of x-ray pulses having different energy levels which collectively create the one or more radioisotope species that define the radioisotope signature. The x-ray source may be an inverse Compton scatter x-ray device. In one embodiment, the x-ray source is configured to irradiate the target with a monochromatic x-ray pulse. The x-ray source may also be configured to irradiate the target with an x-ray pulse or a series of x-ray pulses with each x-ray pulse having a FWHM on the order of 10 picoseconds, a flux of at least $1 \times 10^9$ photons and an energy of at least 15 MeV. In one embodiment, the x-ray source may be disposed at a security checkpoint such that the target may be screened while a radioisotope signature is created therein.

The apparatus of this aspect of the present invention also includes the radiation detector for detecting radiation emitted by the target. In one embodiment, the apparatus includes a plurality of radiation detectors disposed at different respective locations. The apparatus of this aspect of the present inventions also includes a processor for comparing the radiation emitted by the target with a radioisotope signature to permit identification of the target. In the embodiment which includes a plurality of radiation detectors, the processor may be configured to track the target by identifying the target in response to the radiation detected by each of the plurality of radiation detectors.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 2 is a block diagram of an apparatus in accordance with one embodiment of the present invention;

Figure 1:
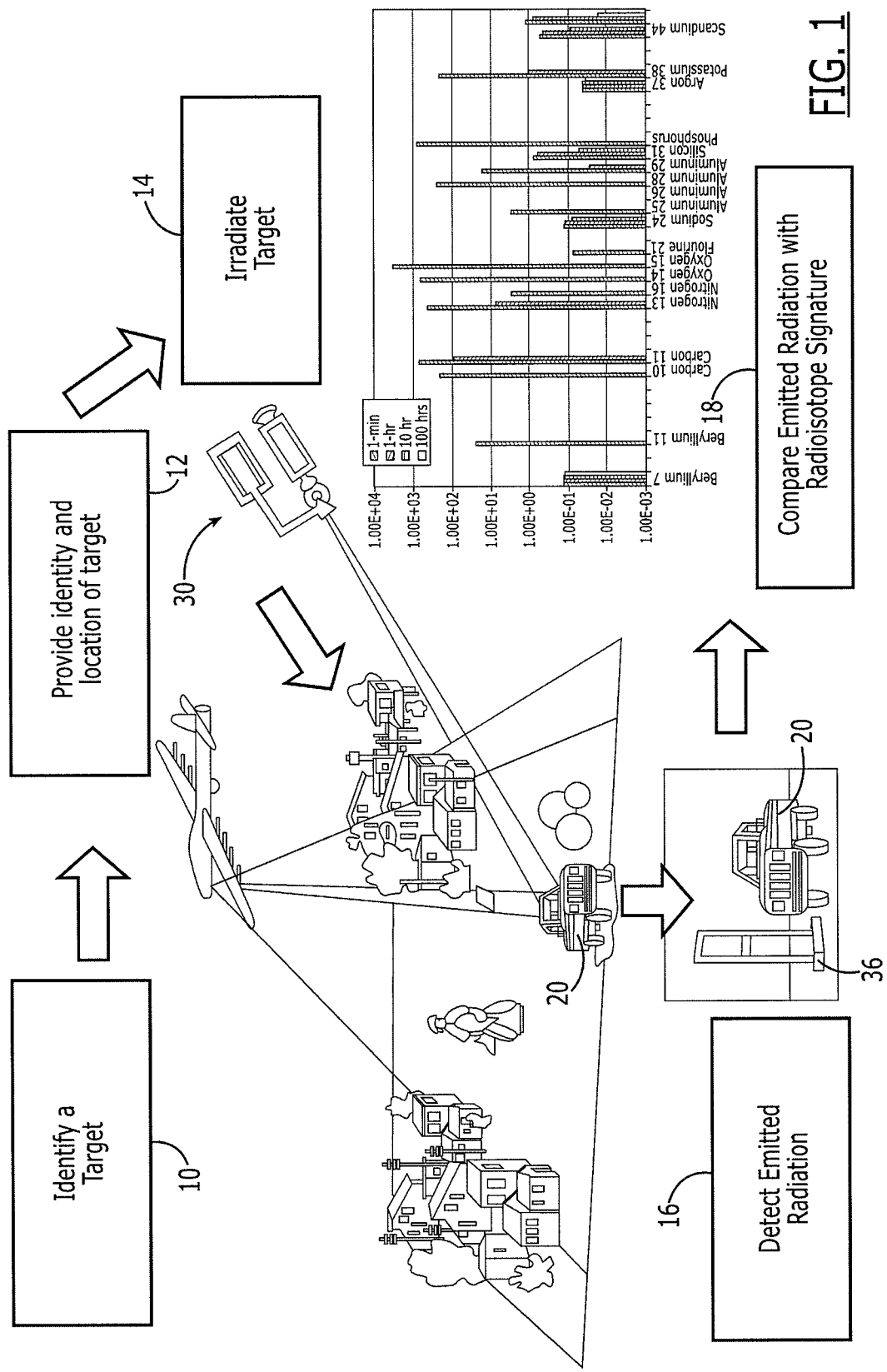
FIG. 1 is a schematic representation of the operations performed in accordance with one embodiment of the present invention.

FIG. 3 is a block diagram of an x-ray source that may be employed by an apparatus in accordance with one embodiment of the present invention; and FIG. 4 is a graphical representation of the radioisotope species created within an individual in response to irradiation by an x-ray pulse having a flux of $1\times10^{10}$ photons and an energy of at least 30 MeV in accordance with one embodiment of the present invention.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Methods and apparatus are provided in accordance with the various embodiments of the present invention for tagging and identifying a target. The target may be either an individual or any of a wide variety of items, such as a vehicle, cargo, weapons or the like. By tagging and thereafter identifying target, the target may be located and tracked. The tracking of the target may be useful in a wide variety of commercial applications, such as the tracking of cargo. However, the method and apparatus of one embodiment of the present invention will be primarily described hereinafter in conjunction with a military, intelligence and/or law enforcement operation in which it is desirable to track an individual or other item.

Regardless of the application, the target is initially identified. In FIG. 1 in which an exemplary application of the method and apparatus of one embodiment is depicted, a target 20 is initially identified as a result of intelligence operations, such as the airborne reconnaissance of the illustrated embodiment. See block 10. Thereafter, the identity and location of the target is provided to an x-ray source 30 and, more typically, to an operator or a computing device that is controlling the operation of the x-ray source. See block 12. Based upon the location of the target, an x-ray pulse is generated and is directed in such a manner as to irradiate the target and to create a radioisotope signature within the target. See block 14.

As shown schematically in FIGS. 1 and 2 and in more detail in FIG. 3, an apparatus 25 in accordance with one embodiment to the present invention includes an x-ray source 30. The x-ray source is configured to irradiate the target 20 with an x-ray pulse. The x-ray pulse is generally a relatively short pulse with high energy x-rays and a narrow "beam-like" output cone. Additionally, the x-ray source advantageously produces a monochromatic pulse. By irradiating the target with a very short, monochromatic pulse, nuclear reactions can be triggered in the target, such as the generation of one or more radioisotope species. By controllably adjusting the energy of the x-rays and/or by applying multiple pulses at different energy levels, different nuclear reactions and, in turn, different radioisotopes (or, at least, different amounts of the same radioisotopes) can be generated within the target. The radioisotopes that are generated within the target define the radioisotope signature of the target. By controllably adjusting the energy level of one or more x-ray pulses with which the target is irradiated, the target may have a unique radioisotope signature.

By employing a monochromatic pulse of x-rays, a measurable radiation spectral signature may be produced in response to irradiation by a relatively low number of incident photons, that is, at a relatively low level of flux. As such, a radioisotope signature may be created for a target 20 without exposing the target to a dangerous level of radiation. For example, a radioisotope signature may be created within the target in response to radiation dose levels that are a few tens of mRs (miliRoentgens), that is, in an amount nominally less than the dose received in a medical diagnostic procedure.

By providing an x-ray pulse having a narrow "beam", the x-ray source 30 permits the radioisotope signature to be applied from a significant standoff distance. As such, the method and apparatus 25 of the embodiments of the present invention may be employed to generate a radioisotope signature within a target 20 in a covert manner so as to tag targets without the knowledge of the target or individuals nearby the target. For example, the x-ray source may be effective to create radioisotope signatures within the target from a standoff distance of several tens of meters and, perhaps, several hundreds of meters. As such, the x-ray source may be carried by an aircraft or other air vehicle. Alternatively, the x-ray source may be located on the ground such as within a security checkpoint. In this regard, a target that is passing through a security checkpoint may be screened for explosive devices or the like, while concurrently being irradiated by an x-ray pulse that creates a radioisotope signature within the target for subsequent tracking purposes.

Although the x-ray source 30 may be configured to generate x-ray pulses having various durations, levels of flux and energy levels, the x-ray source of one embodiment is configured to generate a series of x-ray pulses with each pulse having a full wave half maximum (FWHM) duration on the order of 10 picoseconds or less, a flux of at least $1\times10^9$ photons and an energy of at least 15 MeV. Additionally, the x-ray source of this embodiment may be configured to generate an x-ray pulse having a cone angle of less than about 1 degree.

The x-ray source 10 of one advantageous embodiment is depicted in more detail in FIG. 3. Although the x-ray source may be configured in various manners, the x-ray source of this embodiment is an inverse Compton scatter x-ray device which includes a short pulse electron beam accelerator 32 and a high peak power pulsed laser source 34. The output of the laser source and the electron beam accelerator are directed toward one another with the collision of the electrons and laser output producing an x-ray pulse of the type described above. One example of an inverse Compton scatter x-ray device that may produce a suitable x-ray pulse has been developed by MXI, Inc. of Nashville, Tenn.

Each target irradiated by the x-ray source 30 of one embodiment of the present invention generally has a nuclear reaction cross-section function which is dependent upon the energy of the photons with which the target 20 is irradiated. For example, FIG. 4 depicts seven different radioisotope species that are generated within an individual in response to irradiation by a single pulse having a flux of $1\times10^{10}$ photons and an energy of 30 MeV. As shown, all seven radioisotope species are initially generated and then decay at different rates. As noted above, the radioisotope species that are generated by the x-ray pulse define the radioisotope signature of the target.

Once the x-ray source 30 has generated a radioisotope signature within the target 20, the target may then be identified and tracked based upon its radioisotope signature. As such, the apparatus 10 of one embodiment as shown in FIG. 2 also includes one or more radiation detectors 36 for detecting radiation emitted by the target. See also block 16 of FIG. 1. The apparatus of the embodiment of FIG. 2 also includes a processor 38, such as a microprocessor, an application specific integrated circuit (ASIC) or any other type of computing device, for comparing the radiation emitted by the target to the radioisotope signature to permit identification of the target.

In this regard, the radioisotope signature of the target 20 may be identified immediately or shortly after the irradiation of the target. For example, the x-ray source 30 may irradiate the target with an x-ray pulse and a radiation detector 36 may thereafter detect the radiation emitted by the target. The radiation that is detected may be provided to the processor 38 so as to define the radioisotope signature for the target. In addition to identifying the radiation emitted by the target, one or both of the radiation detector and the processor can identify the time that which the radiation is detected, thereby providing a time stamp for the radioisotope signature. Thereafter, in instances in which the target passes by or within range of a radiation detector as shown in block 16 of FIG. 1, the radiation emitted by the target may be detected and time stamped. By providing the information relating to the radiation that has been detected and the associated time stamp to the processor, the processor can compare the radiation emitted by the target with the radioisotope signature of one or more targets to identify the specific target having a radioisotope signature that matches the radiation emitted by the target. See block 18 of FIG. 1. Depending upon the lapse of time between the irradiation of the target and the subsequent detection of radiation emitted by the target, the processor may compare the radiation emitted by the target to the radioisotope signature by not merely comparing the radiation emitted by the target to the radioisotope signature that was captured immediately or shortly after the irradiation of the target, but by, instead, comparing the radiation emitted by the target to the radioisotope signature of the target after taking into account the decay of the various radioisotopes that were generated by the irradiation of the target. In this regard, the processor can determine the anticipated radioisotope signature of the target by accounting for the decay of the radioisotope species that would have occurred during the period of time between the original irradiation of the target and the subsequent detection of the radiation emitted by the target in accordance with their predefined rates of decay, as shown in FIG. 4, for example, and then comparing the anticipated radioisotope signature with the radiation now emitted by the target.

With reference to FIG. 1, the radioisotope signature of one specific target is graphically depicted. In this regard, the graphical representation of the radioisotope signature depicts the signature at four different points in time following irradiation, namely, one minute after irradiation, one hour after irradiation, ten hours after irradiation and one hundred hours after irradiation. As will be noted, the radioisotope signature will vary over time with some species decreasing markedly or completely over time with other species decreasing very little. In any event, the radiation emitted by the target can be compared to the radioisotope signature of one or more specific targets in an effort to identify the target. In this regard, the radioisotope signature of the specific targets that is employed for comparison purposes can be that version of the radioisotope signature that is expected after taking into account the time lapse since the irradiation of the specific target.

By tagging the target 20 with a radioisotope signature, such as the radioisotope signature that is created within the target in response to irradiation of the target with an x-ray pulse, the target may be subsequently identified by comparing radiation emitted by the target with the radioisotope signature with which the target was tagged. Based upon the identification of the target, the target may be effectively identified, located and tracked in a surreptitious or covert manner.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of tagging and subsequently verifying an identity of a target comprising:
    identifying the target;
    irradiating the identified target with an x-ray pulse to thereby create one or more radioisotope species within the target, wherein irradiating the identified target comprises controllably adjusting an energy level of the x-ray pulse with which the identified target is irradiated to create a unique radioisotope signature for the target;
    initially detecting radiation emitted by the target based upon the one or more radioisotope species created within the target so as to define the unique radioisotope signature for the target;
    identifying a time at which the radiation is initially detected;
    following initial detection of the radiation, subsequently detecting radiation emitted by an individual or an item and identifying a time at which the radiation is subsequently detected;
    determining an anticipated radioisotope signature based upon the unique radioisotope signature for the target and decay of the radioisotope species that were created within the target by said irradiating of the target during a period of time between initially detecting the radiation and subsequently detecting the radiation in accordance with predefined rates of decay for the respective radioisotope species; and
    comparing the radiation emitted by the individual or the item that was subsequently detected with the anticipated radioisotope signature to permit verification of the identity of the individual or the item as the target.

2. A method according to claim 1 wherein irradiating the target comprises irradiating the target with a plurality of x-ray pulses having different energy levels which collectively create the one or more radioisotope species that define the radioisotope signature.

3. A method according to claim 1 wherein subsequently detecting radiation comprises detecting radiation at a plurality of different locations.

4. A method according to claim 3 further comprising tracking the target by identifying the target in response to the radiation detected at each of the plurality of different locations.

5. A method according to claim 1 wherein irradiating the target comprises irradiating the target with at least one x-ray pulse having a flux of at least $1 \times 10^9$ photons and an energy of at least 15 MeV.

6. A method according to claim 1 wherein irradiating the target with the x-ray source comprises irradiating the target with a plurality of x-ray pulses having a full wave half maximum (FWHM) duration of no more than 10 picoseconds.

7. A method of tagging and subsequently verifying an identity of a target comprising:

identifying the target;

tagging the identified target with a unique radioisotope signature, wherein tagging the target comprises irradiating the target with an x-ray pulse to thereby create the unique radioisotope signature comprised of one or more radioisotope species generated within the target by the x-ray pulse, and wherein irradiating the target comprises controllably adjusting an energy level of the x-ray pulse with which the target is irradiated to create the unique radioisotope signature for the target; and subsequently identifying the target by comparing radiation emitted by an individual or an item subsequent to the tagging of the target with an anticipated radioisotope signature of the target wherein subsequently identifying the target comprises:

determining the anticipated radioisotope signature based upon the unique radioisotope signature for the target and decay of the radioisotope species that were created within the target by said irradiating of the target during a period of time between tagging the target with the unique radioisotope signature and subsequently identifying the target in accordance with predefined rates of decay for the respective radioisotope species; and comparing the radiation emitted by the individual or the item subsequent to the tagging of the target with the anticipated radioisotope signature to permit verification of the identity of the individual or the item as the target.

8. A method according to claim 7 wherein irradiating the target comprises irradiating the target with a plurality of x-ray pulses having different energy levels which collectively create the one or more radioisotope species that define the radioisotope signature.

9. A method according to claim 7 wherein identifying the target further comprises detecting radiation emitted by the individual or the item.

10. A method according to claim 9 wherein detecting radiation comprises detecting radiation at a plurality of different locations.

11. A method according to claim 10 further comprising tracking the target by identifying the target in response to the radiation detected at each of the plurality of different locations.

12. A method according to claim 7 wherein tagging the target comprises irradiating the target with a plurality of x-ray pulses having a full wave half maximum (FWHM) duration of no more than 10 picoseconds.

13. A method of tagging and subsequently verifying an identity of a target comprising:

identifying the target;

irradiating the identified target with an x-ray pulse having a controllably adjustable energy level to thereby create one or more radioisotope species within the target, wherein irradiating the identified target comprises controllably adjusting the energy level of the x-ray pulse with which the identified target is irradiated to create a unique radioisotope signature for the target;

initially detecting radiation emitted by the target based upon the one or more radioisotope species created within the target so as to define the unique radioisotope signature for the target;

identifying a time at which the radiation is initially detected;

following initial detection of the radiation, repeatedly detecting radiation emitted by an individual or an item at a plurality of points in time subsequent to the initial detection of the radiation and identifying each time at which the radiation is subsequently detected;

in conjunction with each of the plurality of points in time, determining an anticipated radioisotope signature based upon the unique radioisotope signature for the target and decay of the radioisotope species that were created within the target by said irradiating of the target during a period of time between initially detecting the radiation and subsequently detecting the radiation at a respective point in time in accordance with predefined rates of decay for the respective radioisotope species; and in conjunction with each of the plurality of points in time, comparing the radiation emitted by the individual or the item that was subsequently detected at a respective point in time with the anticipated radioisotope signature at the respective point in time to permit verification of the identity of the individual or the item as the target and tracking of the target.

14. A method according to claim 13 wherein irradiating the target with the x-ray source comprises irradiating the target with a plurality of x-ray pulses having a full wave half maximum (FWHM) duration of no more than 10 picoseconds.

15. A method according to claim 13 wherein repeatedly detecting radiation at the plurality of points in time subsequent to the initial detection of the radiation comprises detecting radiation at a plurality of different locations.

16. A method according to claim 15 further comprising tracking the target by identifying the target in response to the radiation detected at each of the plurality of different locations.

17. A method according to claim 13 wherein irradiating the target comprises irradiating the target with at least one x-ray pulse having a flux of at least $1 \times 10^9$ photons and an energy of at least 15 MeV.

* * * * *